United States Patent [19]

Wang et al.

[11] Patent Number: 4,961,674
[45] Date of Patent: Oct. 9, 1990

[54] DRILL GUIDE FOR PRECISE DRILLING

[76] Inventors: Edward A. Wang, 370 A 2nd Ave., San Francisco, Calif. 94118; George M. Kung, 125 Manor Dr., San Francisco, Calif. 94127

[21] Appl. No.: 384,172

[22] Filed: Jul. 21, 1989

[51] Int. Cl.$^5$ .......................................... B23B 49/00
[52] U.S. Cl. ..................................... 408/14; 408/16; 408/112; 408/241 S
[58] Field of Search .................. 408/14, 97, 99, 100, 408/110, 112, 113, 202, 241 S, 15, 16

[56] References Cited

U.S. PATENT DOCUMENTS

| | | |
|---|---|---|
| 1,058,149 | 4/1913 | Campbell . |
| 1,603,337 | 10/1926 | Gury .................... 408/202 |
| 2,301,151 | 11/1942 | Spievak ................ 408/112 |
| 2,335,614 | 11/1943 | Spievak . |
| 2,382,639 | 3/1945 | Kennard . |
| 2,625,062 | 1/1953 | Heil ...................... 408/112 |
| 2,868,044 | 1/1959 | Chaffee et al. . |
| 3,015,240 | 1/1962 | Hodnett ................ 408/112 |
| 3,083,593 | 4/1963 | Cotter . |
| 3,320,832 | 5/1967 | Jensen . |
| 3,550,481 | 12/1970 | Jensen . |
| 3,620,635 | 11/1971 | DalBianco .......... 408/112 |
| 3,776,647 | 12/1973 | Hart .................. 408/241 G |
| 4,012,161 | 3/1977 | Shultz ................. 408/112 |
| 4,027,992 | 6/1977 | Markey ................ 408/97 |
| 4,290,717 | 9/1981 | Aslen ................ 408/241 G |
| 4,588,334 | 5/1986 | Khurana ................ 408/61 |
| 4,674,927 | 6/1987 | Khurana ................ 408/56 |
| 4,802,798 | 2/1989 | Adamson .............. 408/112 |
| 4,836,720 | 6/1989 | Hadden ................ 408/112 |

FOREIGN PATENT DOCUMENTS

| | | |
|---|---|---|
| 2209668 | 9/1973 | Fed. Rep. of Germany ...... 408/202 |
| 916987 | 12/1946 | France ................. 408/112 |

OTHER PUBLICATIONS

Bray and Templeman, Principles of Screw Fixation Operative Orthopaedics, 1988, 10 pages.
Albrektsson, Jansson and Lekholm, Osseointegrated Dental Implants, 12 Pages.
Goldhahn, Neurosurgical Operation, 1984, 3 Pages.
Karaguiosov, Operative Neurosurgery, 1984, 2 pages.

*Primary Examiner*—Daniel W. Howell

[57] ABSTRACT

A drilling guide for providing stability, direction, force and depth control for precise drilling comprises a hollow shaft attached to drill shaft casing, a telescopic housing connected to hollow shaft with a close coil spring, a depth measuring scale and a set of locknuts as depth controlling device. The threaded portion of hollow shaft provides means for depth measuring and controlling surface and nonthreaded portion and outward flange provides means for direction guidance for the housing. The housing which could protect adjacent objects from drilling relatively moves upwardly during downward movement of hollow shaft and stops at where locknuts are located. The housing comprises a serrated edge for aiding stability and vented holes for exiting drilling byproduct. The close coil spring can provide consistent resistance to prevent unexpected plunging of drill bit and can bring the drill bit back to the original position following the same path of drilling.

2 Claims, 2 Drawing Sheets

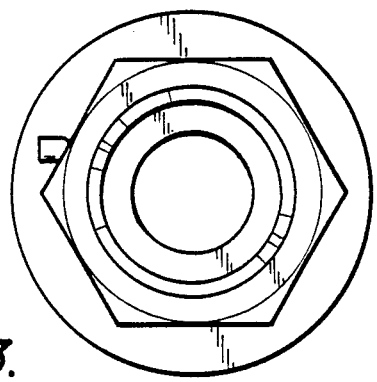
FIG._3.
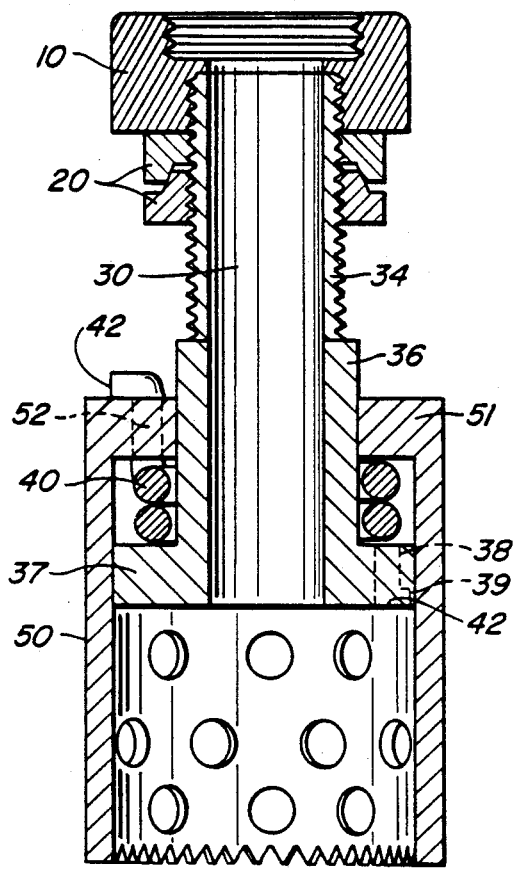
FIG._1.
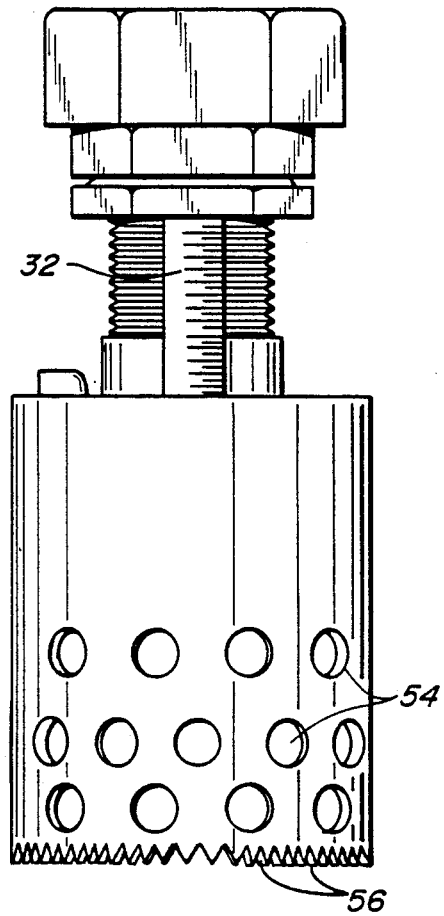
FIG._2.

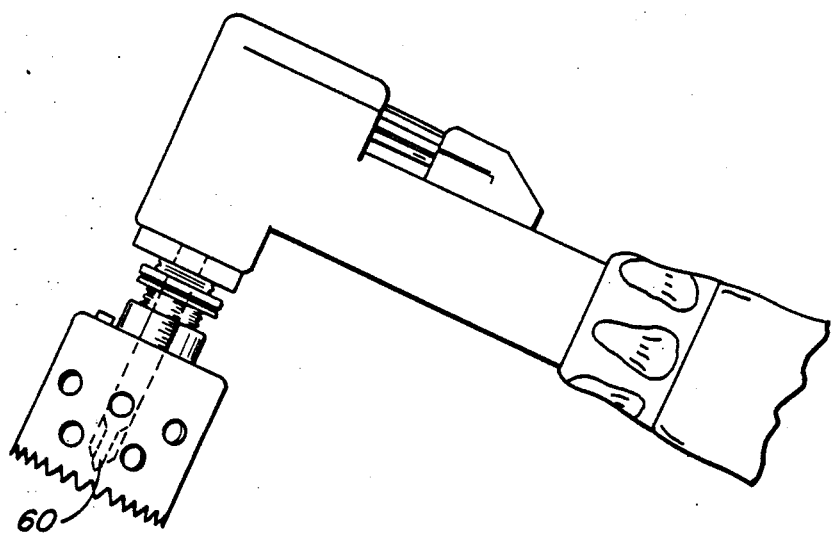
FIG._4.

DRILL GUIDE FOR PRECISE DRILLING

BACKGROUND

1. Field of Invention

This invention is a telescope type of guide relating to drilling, especially an accessory to hand-held drill for use in precisely placing cylindrical holes with direction stability, force and depth control.

2. Description Of Prior Art

Most of surgeons while preparing holes into or through bones by using hand-held drill would likely face common difficulties as other drill users which are difficult direction control, difficult depth control, poor force and stability control.

Because of those poor controls, it is not unusual to overprepare holes in depth and wrong direction which would cause unnecessary traumatic bone injury and lead to delayed healing or failure.

Heretofore a wide variety of guiding instruments have been developed and implemented for drilling control.

In the past. accessories as nose pieces have been used with drills to protect drill bit from damaging and help supporting stability in general drilling. Some nose pieces could also provide certain length adjustment. There was, however, no specific nose piece which could provide stability and direction control over uneven surface, specifically accurate drilling depth control and drilling force control while drilling through different hardness of working piece.

Another type of such instrument which is used in cerebral trephination by neurosurgeons comprised a sharp point guiding pin attached to the shaft of power drill and is used to prevent burr from passing beyond the skull. Surgeons regarded this instrument as unsatisfactory because poor depth control, lack of stability and force control which have forced surgeons using their fingers as additional guard to prevent plunging through the skull.

In orthopaedic surgery, surgeons use other type of instruments comprising a series of drilling sleeves and tap sleeves. Surgeons consider these instruments as unsatisfactory because of lengthy and complicated procedures poor depth and force control.

Most of dental implantologists use depth mark on the shaft of drill to control drilling depth. As far as direction, force and stability are controlled by free hand.

Most surgeons and drill users, therefore, would find it desirable to have an instrument or tool which could provide stability, force, direction and depth control at the same time while drilling with hand-held drill.

OBJECTIVES AND ADVANTAGES

Accordingly we claim the following as our objects and advantages of the invention: to provide an instrument for easily, reliably and precisely guiding drill into or through objects regardless of the contour of objects, to provide maximal stability control and consistent direction guidance in a manner of bringing fulcrum point from finger rest to drilling surface without influencing by shaking hands or torque of drill, to provide steady force control regardless the difference of hardness within objects, and to provide such instrument which could accurately control drilling depth.

In addition we claim the following additional objects and advantages: to provide an instrument which could safely be held by operator or be leaned on any rigid object to insure further stability and direction control, to provide protection of adjacent structures from uncontrolled drilling and to provide an instrument which requires minimal skill and training to use.

Readers will find further objects and advantages of the invention from a consideration of the ensuing description and the accompanying drawings.

DRAWING FIGURES

FIG. 1 shows a perspective back elevation view of such instrument according to invention.

FIG. 2 shows a front elevation view of such instrument.

FIG. 3 shows a top view of such instrument.

FIG. 4 shows a front elevation view of such instrument mounted to a contra-angle of handpiece.

DRAWING REFERENCE NUMERALS 10 connecting nut
20 locknuts
30 hollow shaft
32 graduated scale on 30
34 threaded portion of 30
36 nonthreaded portion of 30
37 outwardly extending flange of 36
38 hole of 37 for 40
39 recess of 37 for 42
40 close coil spring
42 spring end of 40
50 housing
51 inwardly extending flange on 50
52 hole of 51 for 42
54 vent holes of 50
56 serrated edge of 50
60 drill bit

DESCRIPTION

FIG. 1 shows such instrument according to the preferred embodiment of the invention. The instrument comprises a connecting nut 10 which has two sets of female threads in different diameter. This nut 10 connects drill shaft casing with hollow shaft 30 of this instrument (best shown in FIG. 4). The hollow shaft 30 comprises two different portions which are threaded portion 34 and nonthreaded portion 36. The top portion of threads 34 is used for attachment with nut 10 and the rest of threads is used for locknuts 20 to move along. Part of the front surface from threaded portion to nonthreaded portion will be planned to be graduated for depth scale 32 (shown in FIG. 2). The nonthreaded portion 36 comprises a smooth surface shaft and an outwardly extending flange 37 to allow housing 50 which is telescopic to hollow shaft 30 to glide along with. A through hole 38 within flange 37 and a recess 39 on the bottom of flange 37 will allow close coil spring 40 to pass through and lock in. The close coil spring 40 is placed between flanges of housing and hollow shaft (51, 37). The housing 50 comprises serrated edge 56. vented portion 54 and inwardly extending flange 51. The flange 51 glide along hollow shaft 30 will be stopped at a definite length by locknuts 20. The hole 52 within flange 51 will serve as hole 38 to allow spring 40 to pass through and lock on the outer surface of flange 51.

The drill 60 shown in FIG. 4 may be shorter than the length of instrument so that the serrated edge 56 could reach drilling surface first.

OPERATION

The instrument of FIG. 1 will perform a variety of functions for drilling control including stability direction, force and depth control. For mounting this instrument users should insert and engage drill bit 60 into chuck of drill first, then attach hollow shaft 30 to drill shaft casing by using connecting nut 10 so that the hollow shaft 30 will have same axis as the drill shaft.

To provide stability and direction control users should push hollow shaft 30 against drilling surface toward the direction they want to be for several times in order to engage the drilling surface with indentation by serrated edge 56 so that the instrument could be felt minimal mobility and be able to reengage at same direction and position. The users could also use their other hand or fingers to hold the housing 50 or to lean on other object to provide further stability and direction control. The downward pushing pressure during drilling will be converted into downward stabilizing force through tension provided by close coil spring 40 to the housing 50. When drill bit 60 has been reached to the depth as desired it will be brought back to its original position following the path of drilling by the spring 40 after releasing pushing pressure.

Users could precisely control drilling depth by first measuring the distance between the tip of drill bit 60 and the drilling surface. It simply need to push drill bit 60 against drilling surface and measure the distance of upward movement of housing 50 from depth scale 32. Then, users should add this measurement to the desired drilling length and move locknuts 20 to that length of total measurement. This will make the instrument be able to be used on uneven surfaces.

The user will have steady force control because of consistent resistance provided by the spring 40 no matter how the hardness varies within object. The vent portion of housing 54 will provide exit for the drilling dust or irrigant.

While the above description contains many specificities, the reader should not construe these as limitations on the scope of the invention, but merely as exemplification of preferred embodiment. Those skilled in the art will envision many other possible variations are within its scope. For example skilled artisans will readily be able to change the dimensions and material of various embodiments. They can make variations on the connecting nut and depth adjustment mechanism. They can make the serrated edge and vent holes with other design. They can make the internal close coil spring external to hollow shaft. Accordingly the reader is requested to determine the scope of the invention by the appended claims and their legal equivalents, and not by the examples which have been given.

We claim:

1. A drill guiding instrument for use with a drill, which includes means for securing said drill guide to said drill, the said drill guide comprising
   a. an elongated hollow shaft having a threaded portion, a not threaded portion, and a graduated scale which is carved longitudinally on a portion of said threaded and not threaded surfaces,
   b. said not threaded portion of said shaft having an outwardly extended shoulder and a hole within said outwardly extended shoulder,
   c. a housing having an inwardly extended shoulder which is telescopically mounted and encircling over said shaft, and said housing has a hole through said inwardly extended houlder,
   d. a stretchable means which is secured between said housing and said shaft through said holes of said shoulders of said shaft and said housing,
   e. a drill depth limiting means mounted on the said threaded portion of said shaft.

2. The instrument of claim 1 wherein said stretchable means comprises a close coil spring means for resisting the drill bit from plunging into a working piece when there is little resistance from said working piece.

* * * * *

UNITED STATES PATENT AND TRADEMARK OFFICE
CERTIFICATE OF CORRECTION

PATENT NO. : 4,961,674

DATED : Oct. 9, 1990

INVENTOR(S) : Edward S. Wang, George M. Kung

It is certified that error appears in the above-identified patent and that said Letters Patent is hereby corrected as shown below:

Title page, line 3, change "A. Wang" to --S. Wang--.

Signed and Sealed this

Third Day of March, 1992

Attest:

HARRY F. MANBECK, JR.

*Attesting Officer*  *Commissioner of Patents and Trademarks*